(12) United States Patent
Shay

(10) Patent No.: US 11,616,874 B2
(45) Date of Patent: Mar. 28, 2023

(54) METHOD AND SYSTEM FOR REDUCING THE INSTANCES OF SUICIDE

(71) Applicant: Dustin Adam Shay, Gardner, KS (US)

(72) Inventor: Dustin Adam Shay, Gardner, KS (US)

( * ) Notice: Subject to any disclaimer, the term of this patent is extended or adjusted under 35 U.S.C. 154(b) by 154 days.

(21) Appl. No.: 17/226,036

(22) Filed: Apr. 8, 2021

(65) Prior Publication Data
US 2022/0329683 A1    Oct. 13, 2022

(51) Int. Cl.
| H04M 1/72424 | (2021.01) |
| G06F 3/0488 | (2022.01) |
| H04W 4/029 | (2018.01) |
| G16H 20/70 | (2018.01) |
| G16H 80/00 | (2018.01) |

(52) U.S. Cl.
CPC ...... *H04M 1/72424* (2021.01); *G06F 3/0488* (2013.01); *G16H 20/70* (2018.01); *H04W 4/029* (2018.02); *G16H 80/00* (2018.01)

(58) Field of Classification Search
CPC ......... H04M 1/72424; H04M 1/72457; H04M 2250/22; G06F 3/0488; G06F 3/04847; G16H 20/70; G16H 80/00; G16H 40/20; G16H 40/67; H04W 4/029
See application file for complete search history.

(56) References Cited

U.S. PATENT DOCUMENTS

| 11,424,030 B1* | 8/2022 | Saffouri | G16H 40/67 |
| 2011/0003576 A1* | 1/2011 | Sun | H04W 8/183 |
| | | | 455/404.1 |
| 2018/0020315 A1* | 1/2018 | Guo | H04L 63/083 |
| 2022/0141917 A1* | 5/2022 | Sanghavi | H04W 76/40 |
| | | | 455/3.05 |
| 2022/0157451 A1* | 5/2022 | Elliot | H04M 3/5116 |
| 2022/0303724 A1* | 9/2022 | Ahrens | G08B 25/006 |

OTHER PUBLICATIONS

Martinego, "Suicide prevention and depression apps' suicide risk assessment and management: a systematic assessment of adherence to clinical guidelines," BMC Medicine, p. 2-12.
Nock, "Cross-national prevalence and risk factors for suicidal ideation, plans and attempts," The British Journal of Psychiatry, 2008, p. 98-105, vol. 192, BJPsych.

(Continued)

*Primary Examiner* — Brandon J Miller
(74) *Attorney, Agent, or Firm* — Jesse J. Camacho

(57) ABSTRACT

A computing device is described that receives input from a distressed user that indicates the user is in a state of distress. The computing device references a profiles database that stores attribute information that indicates preferred attributes of a potential responder. The communication is sent to a plurality of responding devices and includes an alert indication, at some of the preferred attributes, and a location of the first computing device. Incident to sending the alert, the computing device receives an acknowledgement that indicates that at least one responsive computing device received the alert, which is associated with a responsive user who has attributes matching the preferred attributes. Presenting a map on the computing device that is useable to help locate the first computing device.

7 Claims, 13 Drawing Sheets

(56) References Cited

OTHER PUBLICATIONS

Gaynes, "Screening for Suicide Risk in Adults: A Summary of the Evidence for the U.S. Preventive Services Task Force," Annals of Internal Medicine, May 18, 2004.

Pearson, "Primary care contact prior to suicide in individuals with mental illness," British Journal of General Practice, Mar. or Nov. 2009, pp. 825-832, vol. 59.

Richards, "Understanding Why Patients May Not Report Suicidal Ideation at a Health Care Visit Prior to a Suicide Attempt: A Qualitative Study," Psychiatric Services, Jan. 2019, pp. 40-45, vol. 70:1.

Frey, Abstract, "Perceptions of Suicide Stigma How Do Social Networks and Treatment Providers Compare?," Abstract, 2015 or 2016, 37, pp. 95-103.

Bruffaerts, "Treatment of suicidal people around the world," The British Journal of Psychiatry, 2011, pp. 64-70, vol. 199.

Yurcaba, "New Law Establishes 988 As National Suicide Hotline," Mental Health News, Oct. 26, 2020, https://www.verywellmind.com/new-law-establishes-988-as-national-suicide-hotline-5083955?print.

CDC, "Suicide rates rising across the U.S. | Comprehensive prevention goes beyond a focus on mental health concerns," Centers for Disease Control and Prevention, Jun. 7, 2018.

* cited by examiner

METHOD AND SYSTEM FOR REDUCING THE INSTANCES OF SUICIDE

BACKGROUND OF THE INVENTION

The field on invention relates to technology to reduce the instances of suicide. The National Institute of Mental Health has reported that, according to the Centers for Disease Control and Prevention (CDC) WISQARS Leading Causes of Death Reports, in 2018: suicide was the tenth leading cause of death overall in the United States, claiming the lives of over 48,000 people. In the past, a person contemplating suicide might have the option of calling a suicide hotline or maybe even a trusted friend. But suicide hotlines do not allow for physical in-person interaction and require the individual to memorize the hotline's phone number. And a friend might be unavailable.

Current technologies are not adequate to efficiently, effectively, and immediately help someone who is struggling with thoughts of suicide. Calling into a call center is unfavorable because many people have become used to or desire real-time help. Calls to call centers can go unanswered due to volume, poor technology, or lack of capacity. It can be devastating if a vulnerable individual's call is not answered. The current technology is limited by location the lack of potential for in-person communication. Moreover, some call-center employees might not be particularly interested in rendering aid to a vulnerable person (instead, mostly available because it is "just a job" or "just a paycheck"). A responder who is not overly interested in the wellbeing of distressed person can also lead to devastating consequences.

The state of the art could be improved by providing an improved computing device that is programmed to present a set of options to a distressed person, receiving input from a user that indicates a preference, and programmatically responds to the preference. The art could further be improved by enabling a selection of a set of preferences that indicate attributes of preferred responders who might respond to an alert communicated by the improved computing device and conveying a location of a distressed user to a potential responder's computing device. In this way, people register to respond to vulnerable people and are available to physically meet with them in real-time.

BRIEF SUMMARY OF THE INVENTION

The claims appended hereto define the scope of the invention. In summary, one embodiment of the invention includes one or more non-transitory computer readable storage media that store at least one program to assist a distressed person. The program includes instructions that, when executed by a receiving computing device with a display, a touch-responsive surface and one or more sensors to detect a touch interaction with the touch-sensitive surface, cause the receiving computing device to perform a method. An embodiment of that method includes receiving a input from a distressed user that is indicative of the user being in a state distress. The method further includes referencing a profiles database that stores attribute information that indicates one or more attributes of potential responsive users.

Additionally, an embodiment of the method includes sending a first electronic communication through an antenna of said first computing device, wherein the electronic communication includes (1) an indication alert indicative of the state of distress; (2) at least a portion of the first attribute information; and (3) a location of said first computing device. In response to the sending of the first electronic communication, the method includes receiving (at the first computing device) an acknowledgment indication that indicates that at least one responsive user received the first electronic communication. The responsive user is associated with a second computing device that is associated with a set of responsive-user attributes and the responsive-user attributes include said at least a portion of the first attribute information. The acknowledgement indication would have been received at the first computing device in response to an electronic instruction provided by the second computing device.

The method also includes causing a location indication to be presented on a display of the second computing device. The location indication indicates the location of the first computing device, enabling the user of the second computing device to locate and render aid to the user of the first computing device.

DETAILED DESCRIPTION OF EMBODIMENTS OF THE INVENTION

Figure 1:
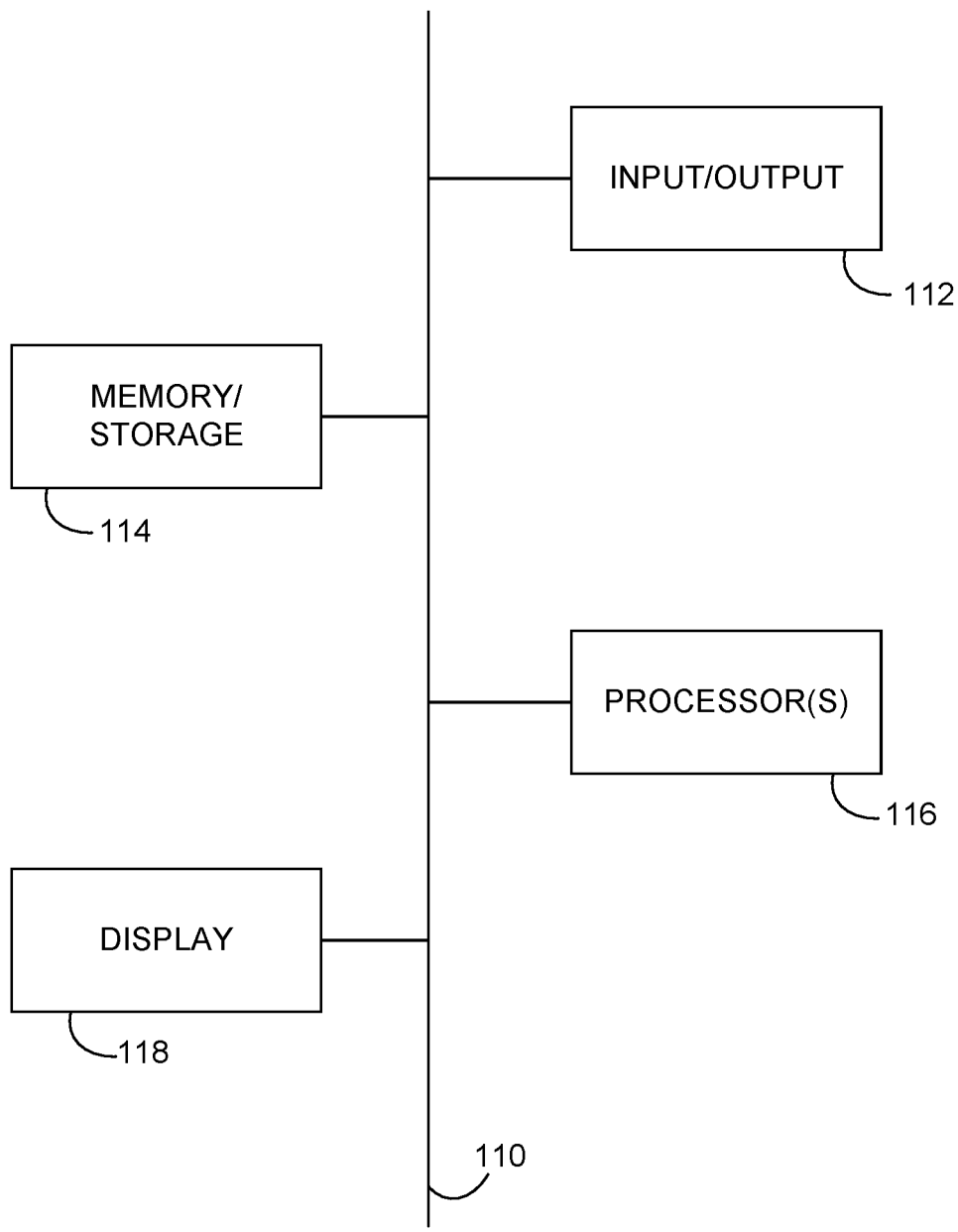
FIG. 1 depicts an illustrates aspects of computing device suitable for practicing an embodiment of the invention.

Figure one depicts an illustrative computing device suitable for practicing an embodiment of the present invention and is generally referenced by the numeral 100. The computing device could take the form of a smart phone, portable electronics device, etc. It includes a bus 110 that communicatively couples one or more input output devices 112 to one or more storage components 114, processors 116, and at least one display 118. Computing device 100 could include a number of other items as well. Paragraph examples of input/output devices 112 include items such as a microphone, speaker, touch screen, keyboard, volume controls, wired or wireless communication components (such as Wi-Fi components, a GPS radio, a Bluetooth radio, a near-field communications component, etc.). One embodiment of the input/slash output devices includes a touch sensitive surface. The touch-sensitive surface is responsive to interaction with the display 118. Input/output devices 112 also include one or more sensors to detect touch interaction in connection with the touch-sensitive surface.

Memory component 114 includes one or more non-transitory computer readable storage media. It includes memory such as random access memory as well as non-volatile long-term storage memory. Storage component 114 is suitable for storing items such as one or more databases, which will be discussed below. Storage component 114 is suitable for storing a program in accordance with an embodiment of the present invention. Such a program includes instructions that, when executed by computing device 100, cause it to perform a series of steps that will be discussed in greater detail below.

Processing component 116 includes one or more processors that process the aforementioned one or more programs that are composed of and include computer executable instructions. In referencing "computer" executable instructions, it is to be understood that the instructions may be performed by any machine with the requisite hardware to process them. Processing component 116 includes processors to process programmatic instructions, video-related instructions, audio-related instructions, instructions associated with the input/output devices 112, and otherwise read and write to memory component(s) 114.

Display 118 is a display component suitable for presenting information to a user and, as mentioned, usable for interacting with components to receive touch-sensitive input. Display component 118 takes the form of a display of a smartphone in one embodiment. Coupled with said display, a digitizer, in one embodiment, process touch-sensitive information.

Figure 2:
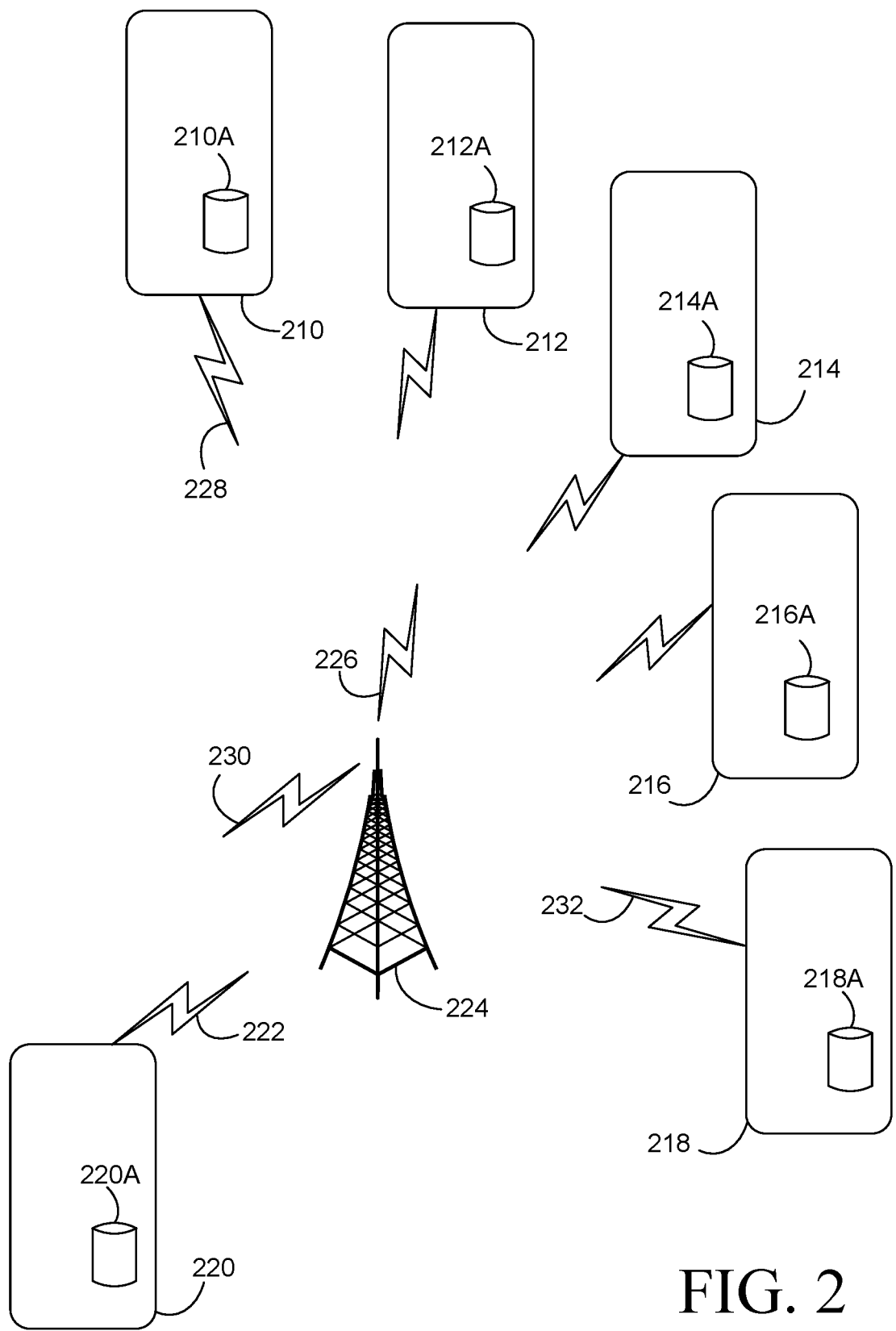
FIG. 2 depicts an illustrative operating environment suitable for practicing an embodiment of the invention.

FIG. 2 depicts an illustrative operating environment that includes a plurality of communication devices that interact with each other through a communications network or directly with each other. The communication devices are reference by numerals 210, 212, 214, 216, 218, and 220. Each of the aforementioned communications devices could take the form of the computing device 100 as described in connection with FIG. 1. Each of the computing devices 210-220 include respective databases 210A comma 212A, 214A, 216A, 218A, and 220A.

Each of the aforementioned database components may include one or more databases that store information or instructions usable to carry out the programmatic instructions of the invention. In some embodiments, the database is local to its respective computing device, while in others it is remote (but still associated with their respective computing device). The various lightning bolts in FIG. 2 illustrate wireless communications that are facilitated by the computing devices.

For example, computing device 220 could send information by way of a wireless signal 222A to a communications tower 224, which by way of a wireless communications signal 226, communicates information to computing device 210. In return, communications device 210 responds with a responsive signal 228 that leads to another responsive signal 230 that is communicated to computing device 220. This communications environment of FIG. 2 is illustrative in nature. In some embodiments, a communications network is not employed. In that scenario, a peer-to-peer communications methodology is utilized, or other similar technology, so as to facilitate direct communication between one or more communications devices shown. For example, signal 222 might be a Bluetooth signal or near field communications signal that interacts directly with computing device 218 and corresponding signals represented by lightning bolt 232.

Figure 3:
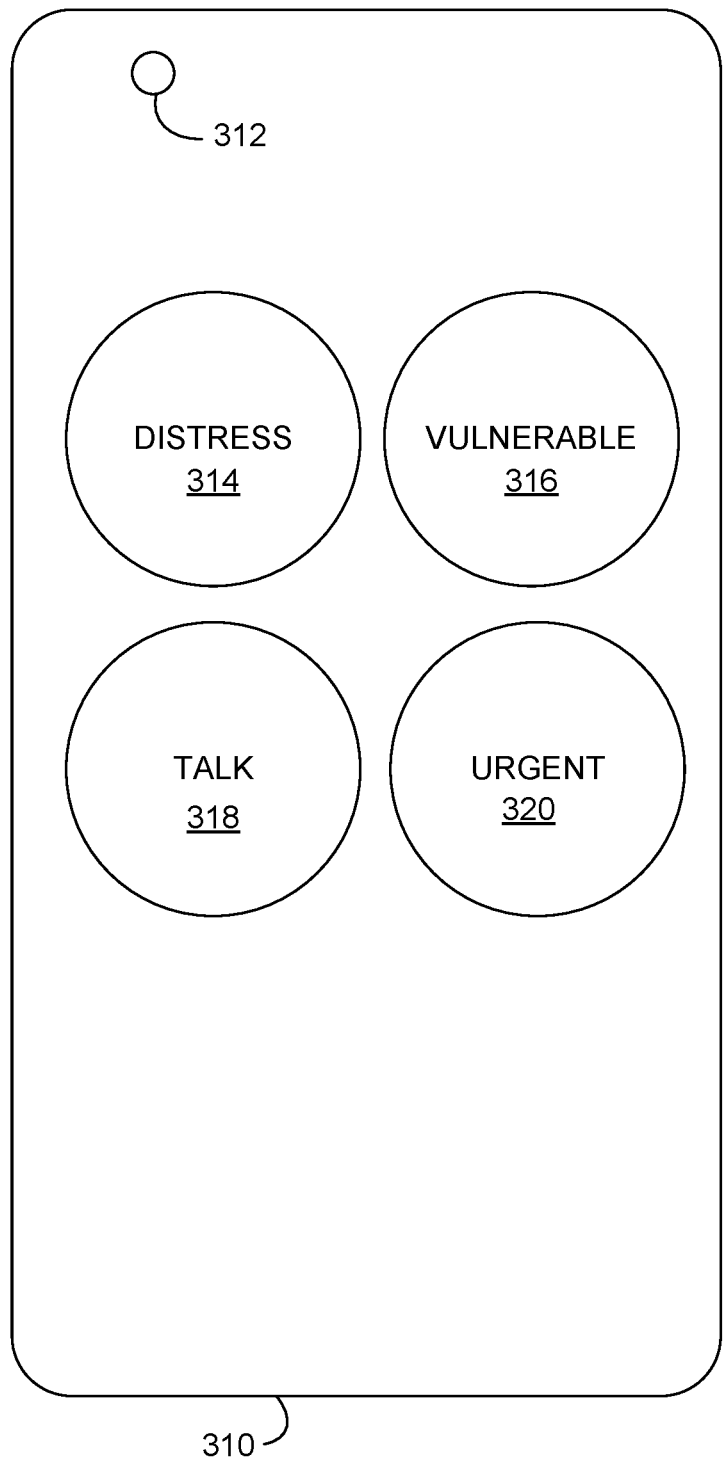
FIG. 3 depicts an illustrative using interface that includes illustrative user-interactive controls to convey input and output in accordance with an embodiment of the invention.

FIG. 3 depicts another illustrative computing device 310 that includes a user interface and several user-interface components. In this embodiment, a user-interface component takes the form of a visual control that can be interacted with by a user so as to provide input or output information to or from computing device 310. Computing device 310 includes a light source 312 and some embodiments. A first illustrative control includes a "distress" control 314. Other controls include a "level-of-vulnerability" control 316, a "talk" control 318, and an "urgent" control 320.

"Distress" control 314 is usable too convey that a user is in a state of distress. For example, a user who might be contemplating thoughts of suicide can press the "distress" button 314 to indicate that he or she is in a state of distress. Control 314 can take the form of a stop sign in one embodiment, with words such as "stop," "don't," or "I would like help.")

Multiple options are provided for a user to indicate his or her level of distress. For example, a "vulnerable" control 316 indicates that the user is feeling vulnerable, but not necessarily in an overwhelming state of distress. This disclosure is not intended to create a strong demarcation between a state of distress and a state of vulnerability. They overlap. Aspects of the invention are being provided to help describe illustrative functionality. For example, users might feel more comfortable indicating that they are merely vulnerable instead of contemplating suicide (even though they might be).

"Talk" control 318 is usable to indicate a desire to talk to avoid or act on feelings that are harmful or self-destructive to themselves. "Talk" control 318 does not provide an ability to communicate with anyone. Rather, it is usable to indicate one's desire to talk with someone. An "urgent" control 320 is usable too convey a sense of urgency. In one embodiment, "urgent" control 320 indicates that a user associated with device 310 is in urgent need of assistance. Other controls could be added without departing from the scope of the present invention.

Figure 4:
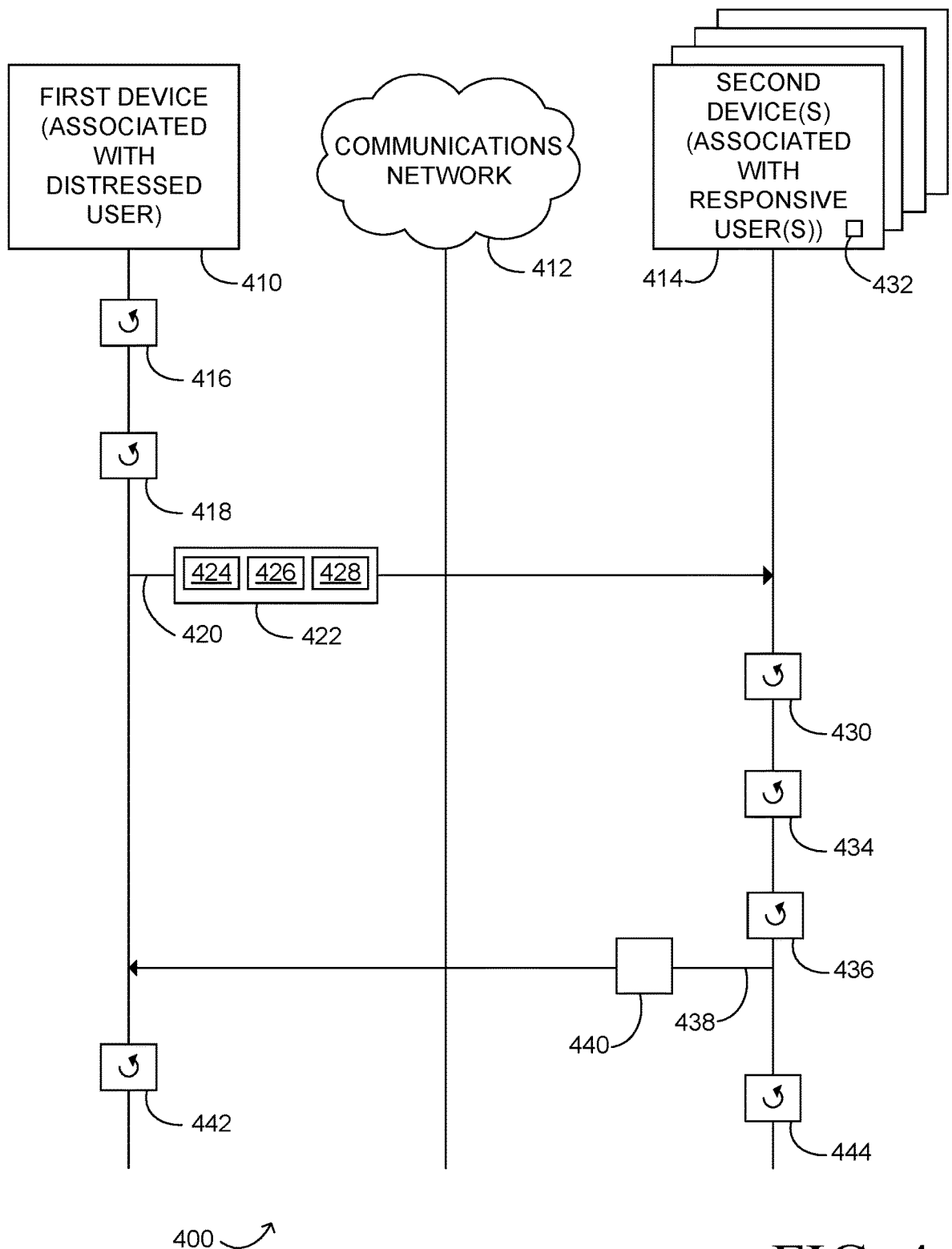
FIG. 4 is a flow diagram that depicts process steps in accordance with an embodiment of the invention.

FIG. 4 depicts an illustrative set of steps in accordance with an embodiment of the present invention and is generally referenced by the numeral 400. FIG. 4 refers to a first computing device 410 that is associated with a distressed user. FIG. 4 also illustrates a communications network 412 that is usable to communicate with one or more second computing devices 414, wherein each of the second computing devices are respectively associated with responsive users. First computing device 410 and second computing device 414 could take the form of computing device 100 or the different computing devices depicted in FIG. 2.

In one embodiment, first computing device 410 includes one or more non-transitory computer readable storage media that store at least one program. The one or more programs include instructions that, when executed by the computing device cause it to perform a series of steps that will be explained below. As mentioned, the first computing device 410 includes a touch-responsive surface and one or more sensors to detect a touch interaction with the touch-sensitive surface of the device in one embodiment.

Reference will be made to a second computing device (in the singular) 414 for readability. But it is understood, and graphically depicted, that item 414 is representative of a plurality of computing devices that could provide information to first device 410. The number of second computing devices could be 2, 2000, or tens or hundreds of thousands of devices or more.

Figure 6:
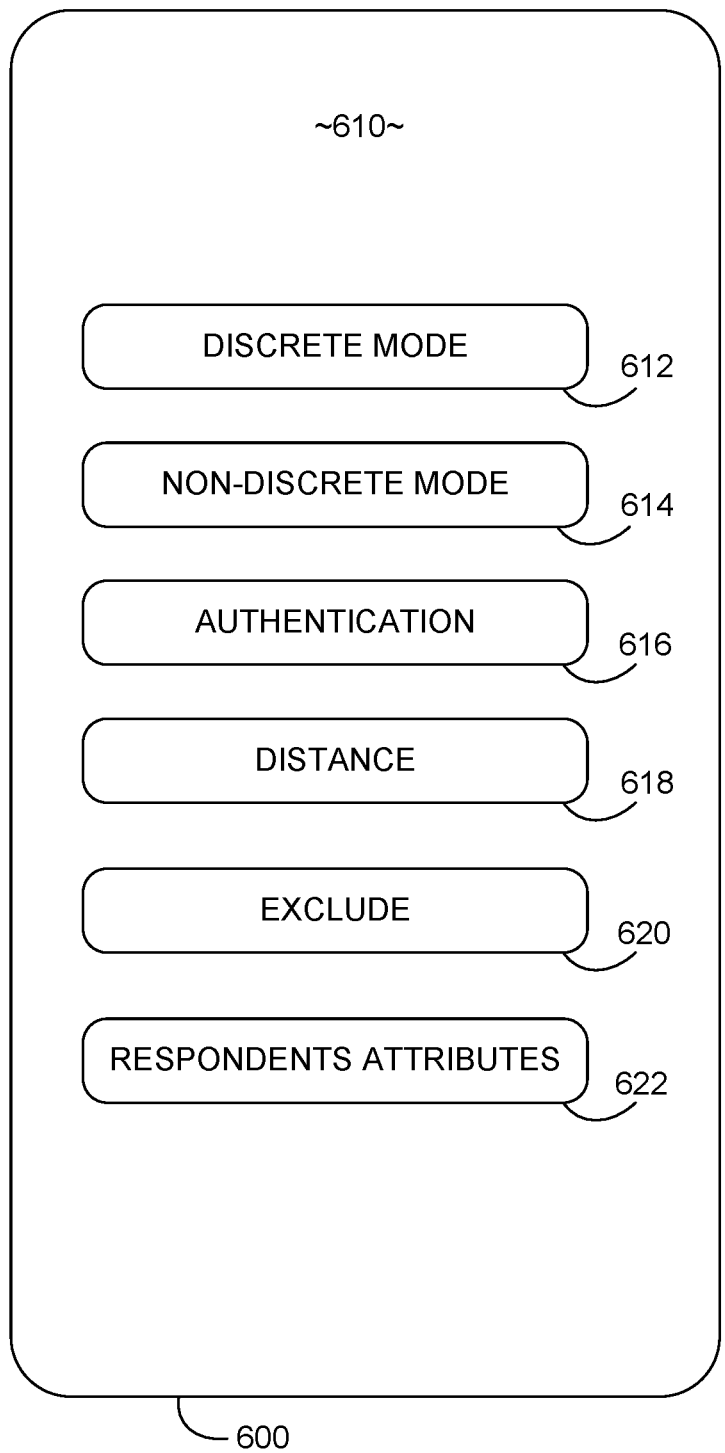
FIGS. 6 and 7 depict other user interfaces with set of controls that are suitable for conveying input/output options in accordance with an embodiment of the invention.
Figure 7:
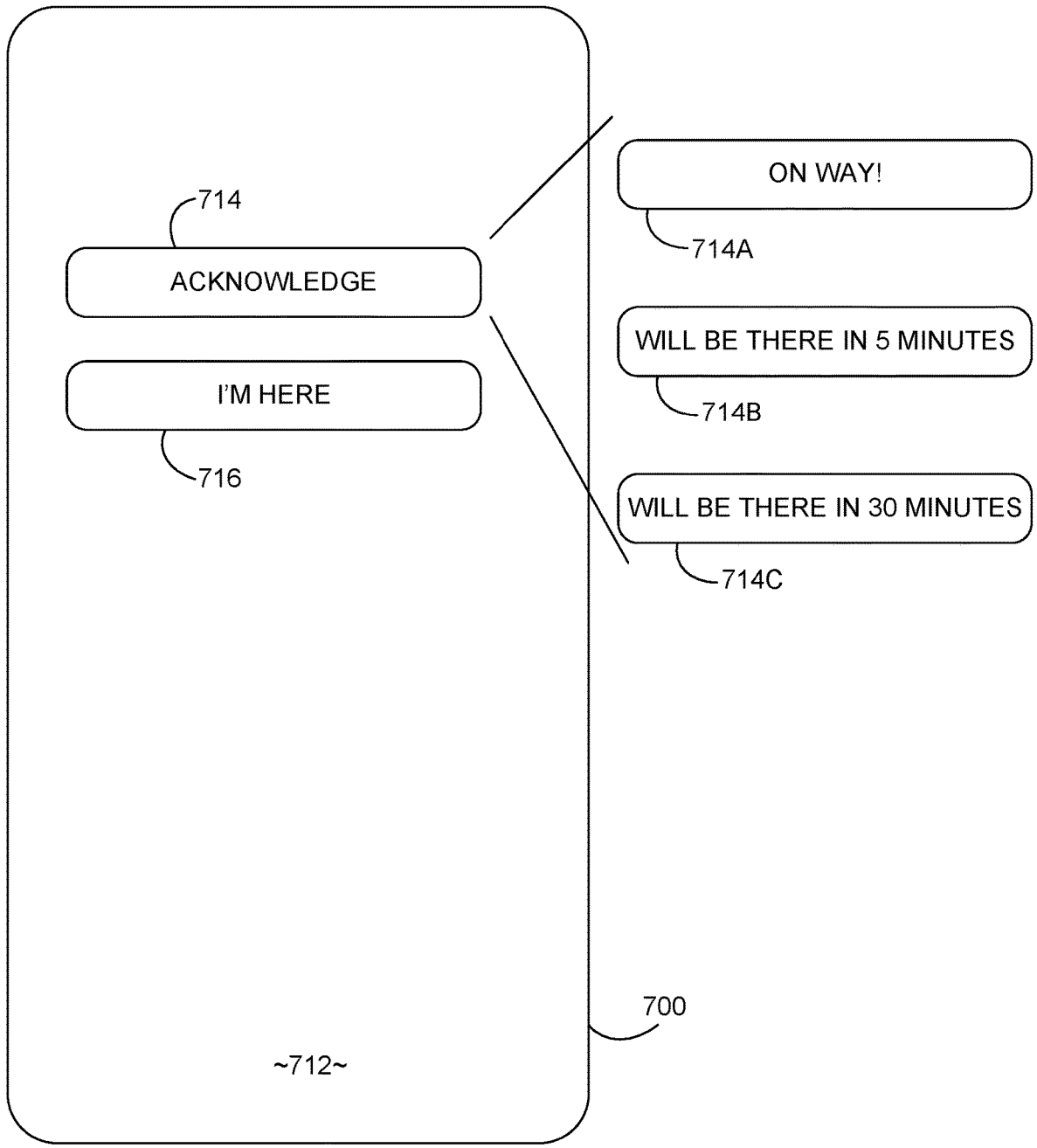

At a step 416, first device 410 receives a first input from a distressed user that is indicative of the user being in a state of distress. That input could be provided by way of a user interface such as the one depicted in FIG. 3. It could also be user input provided by way of a user interface control that is depicted in FIGS. 5-7.

At a step 418, first device 410 references a first profiles database that stores attribute information that indicates a set of desired attributes of potential responsive users. The database could be of the sort previously described in connection with FIG. 2. One of the points of the profiles database is to be sensitive to the desires or wishes of a distressed user. It may be the case that a distressed user is more comfortable talking to people with some attributes as opposed to others. For example, it might be the case that a female would feel more comfortable interacting with a female in a vulnerable state. It might be the case that a person of a certain age would feel more comfortable interacting with a person of the same or of a specific age. It may be the case that a person of a certain religious persuasion word rather interact, in a vulnerable state, with a responsive user of a similar religious persuasion. Thus, the profiles database stores information associated with a gender, a religious preference, and age range, an indication as to whether someone is a professional or not, a family member, or a friend. Other attributes could be included as well.

At a step 420, an electronic communication 422 is communicated from first device 410 to second device 414. In one environment, electronic communication 422 includes an indication alert 424 that is indicative of the aforementioned state of distress, at least a portion of the aforementioned attribute information 426, and a location of first computing device 410. Attribute information 426 can include some or all of the attribute preferences of the distressed user.

As previously mentioned, at step 416, user input is received by way of computing device 410. Such input is received by way of a discrete-input control in one embodiment. The discrete-input control indicates only one of two values. Illustrative discrete-input controls are depicted in FIG. 3. For example "distress" control 314 might include only one of two values: on or off; where "on" indicates a button press and "off" indicates the lack of a button press. Alternatively, the input could be received by way of a variable input control that will be described in connection with FIGS. 5A-5C. As will be explained in greater detail below, the variable input control can indicate a range of values wherein each value corresponds to a level of distress that the distressed user is feeling.

With continuing reference to FIG. 4, at a step 430, second device 414 compares the desired attributes 424 with a set of responder attributes. The responder attributes are represented by numeral 432. Responder attributes 432 are attributes associated with a user who is associated with second device 414. For example, if a responsive user is a female between the ages of 25 through 30, then those attributes will be stored as part of attributes 432 in one embodiment.

A determination is made at a step 434 as to whether the attributes sent and communication 422 sufficiently correspond to the attributes 432 associated with second device 414. In one embodiment, it is sufficient if all of attributes in communication 422 are found in attributes 432. In other embodiments, only a subset of the attributes in communication 422 need to be found in attributes 432 for processing to continue. This can be set by a setting in either or both of first device 410 or second device 414.

If the attributes sufficiently match each other, then at a step 436, second device 414 presents a user interface on its display. In one embodiment, the user interface includes one or more controls that, if acted on, send an acknowledgement to first device 410 from second device 414. At a step 438, a responsive communication 440 is communicated from second device 414 to first device 410. In one embodiment, the responsive communication 440 includes the aforementioned acknowledgement. Communication 440 could include additional information as well. Such additional information includes, for example, an indication as to when the responsive person is on his or her way.

At a step 442, first device 410 presents a confirmation that communication 440 was received by first device 410. In response to first device 410 sending first electronic communication 422, it ultimately receives an acknowledgement indication that is or is part of communication 440 and that indicates that at least one responsive user received first communication 422. The responsive user is associated with second device 414, which, as mentioned, is associated with a set of responsive-user attributes 432. In one environment, the responsive-user attributes 432 include at least a portion of the attributes communicated by way of communication 422. The acknowledgement indication 440 will be received at first device 410.

At a step 444, a location indication is presented on a display of second device 414. The location indication indicates the location of first computing device 410. Likewise, a location indication can be presented on first device 410 that indicates a location of the second computing device 414. The distressed user, utilizing first device 410, can also request additional information from the responsive user. For example, the first device 410 could request additional attribute information, which could be sent by way of second device 414. In this way, and even if additional information is not requested, first device 410 can indicate an acceptance or rejection option, which would either accept or reject the responsive user's indication that he or she is on their way.

At anytime, if desired, first device 410 can cancel the alert, which would result in preventing the location of first device 410 from being presented on second device 414. The entire process can also be anonymized so that neither first device 410 or second device 414 becomes aware of personal identifying information associated with either device.

Figure 5A:
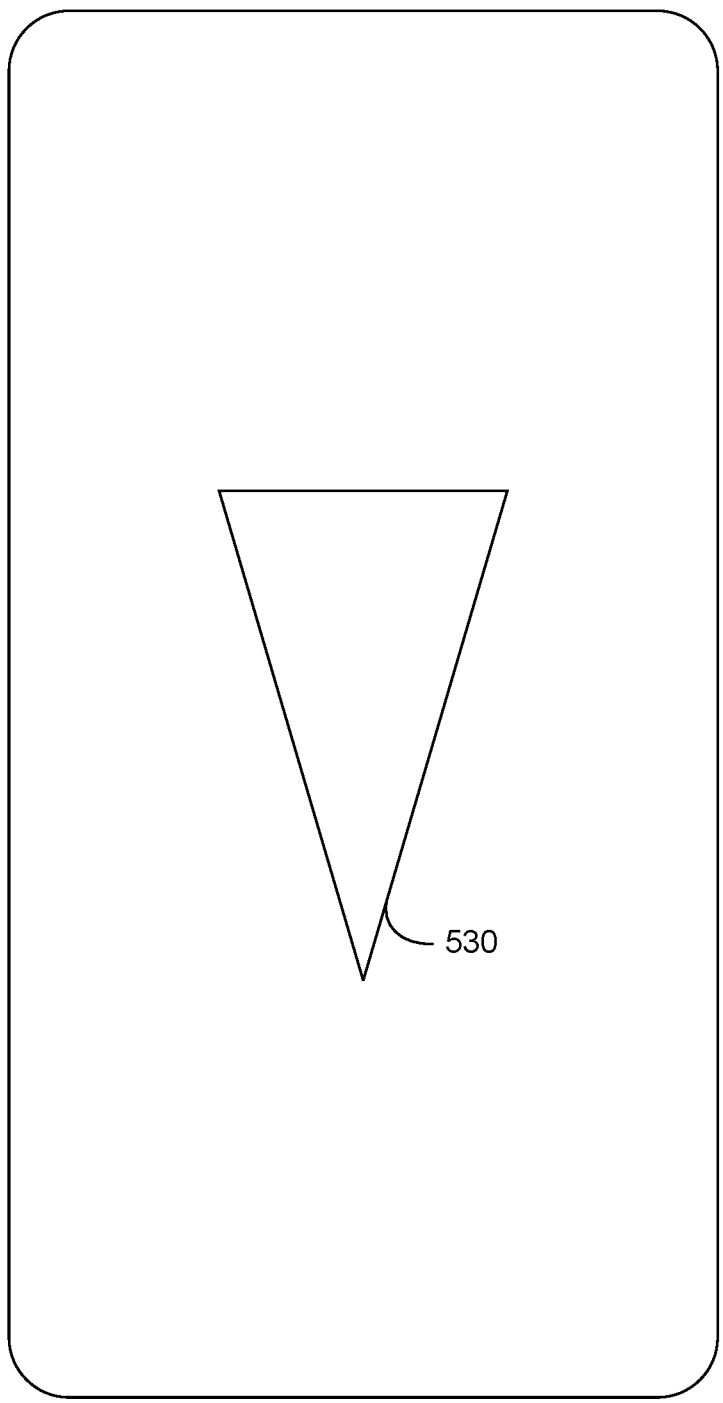
FIGS. 5A-5C depict various states of an electronic user-interface control suitable for indicating a degree of distress that a user is feeling.

FIG. 5A depicts an illustrative user-interface control 530 that is usable by said first computing device to indicate a level or severity of distress. User-interface control 530 could take on a variety of forms. While it is illustratively shown as an inverted triangle, it could take the form of a rectangle, circular shape, or other shape. In one embodiment, it 530 is usable to provide a variable input whose value corresponds to a value manipulated by a user using the touch-sensitive surface. In this way, control 530 can indicate a range of values, wherein each value corresponds to a level of distress that the user is feeling. It can be a slider control that indicates the value within a range of values by way of user input.

Figure 5B:
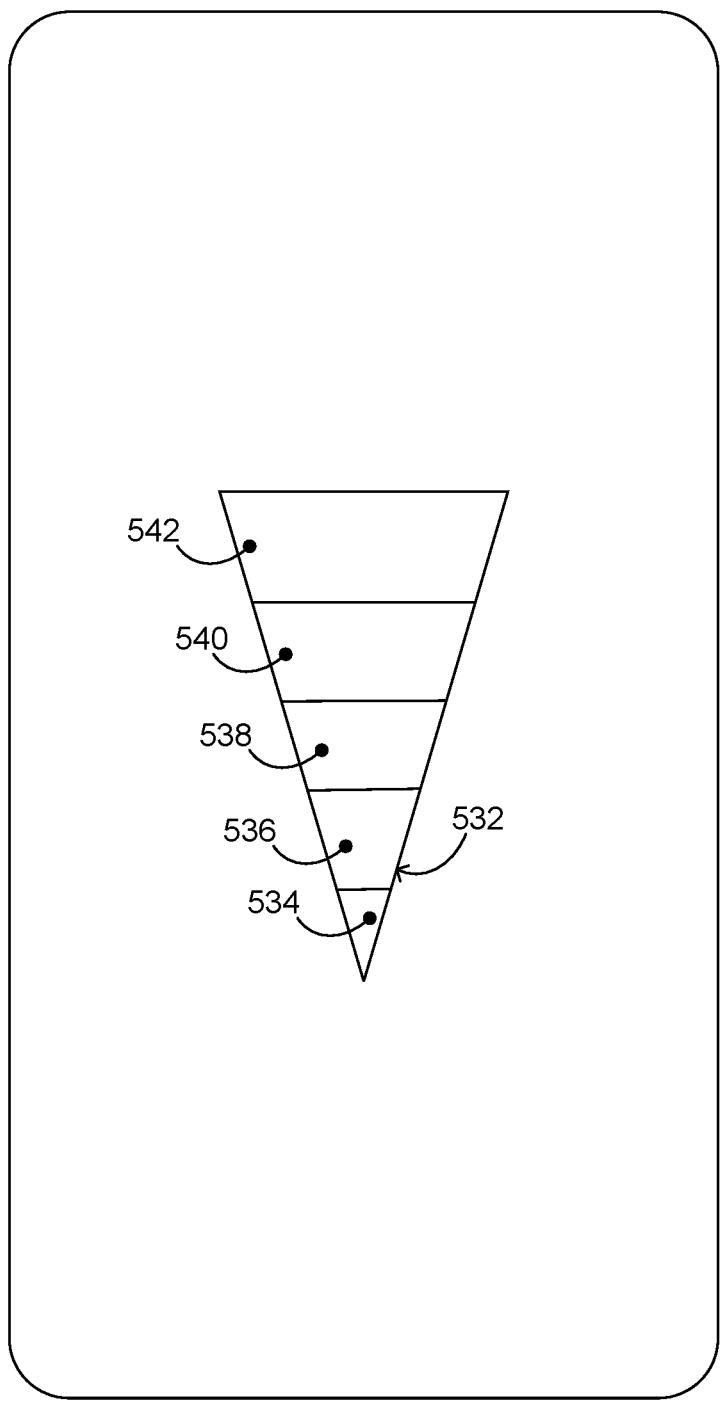

FIG. 5B indicates another version of the user-interface control of FIG. 5A. Here, it is represented by numeral 532. Control 532 shows five illustrative levels of distress as indicated by numerals 534, 536, 538, 540, and 542. There could be additional levels as well. The control 532 can be continuously variable.

Figure 5C:
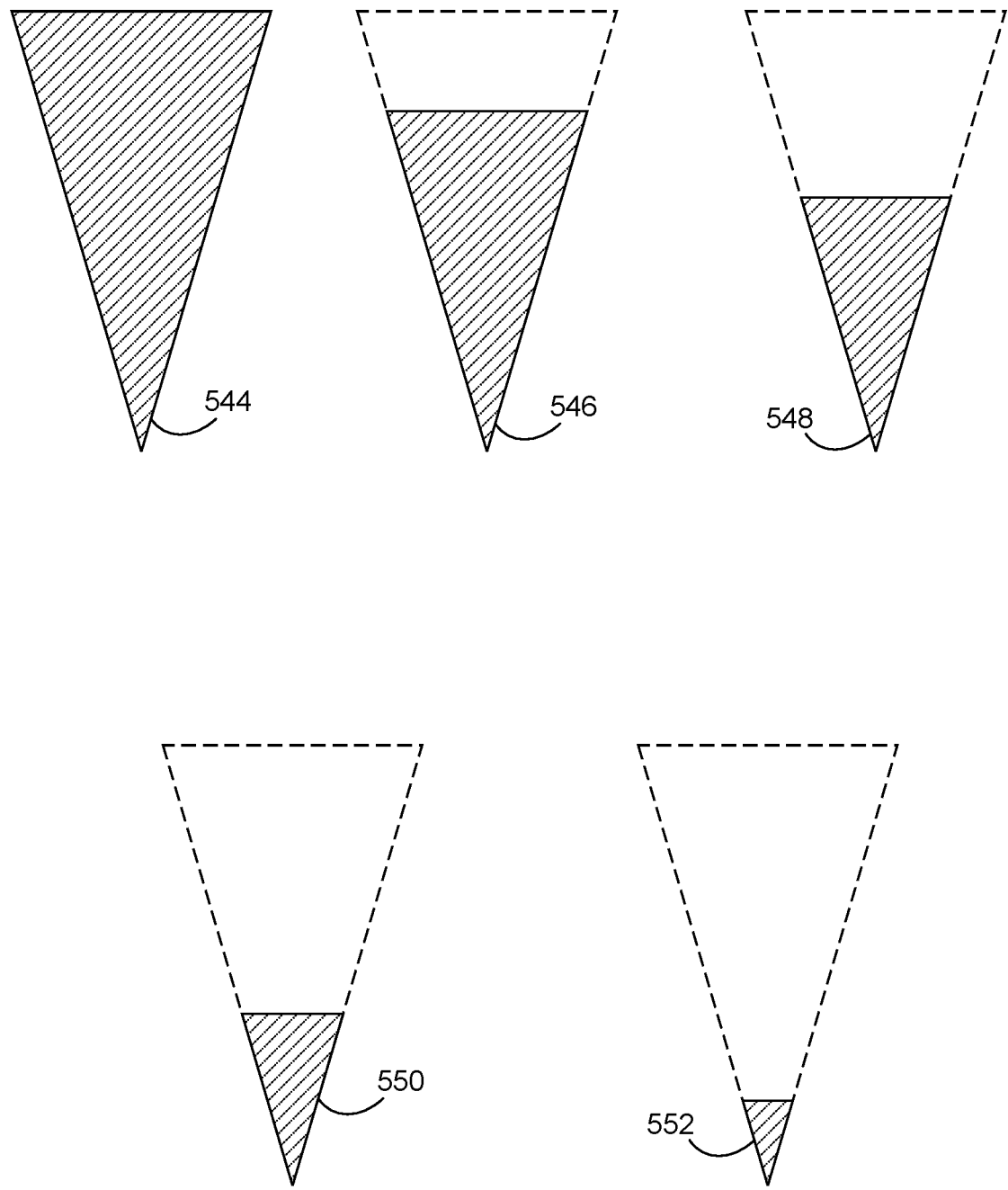

FIG. 5C depicts illustrative feedback options associated with control 530 or 532. For example, control 544 indicates a slider whose position has been slid all the way maximum such that it is solid, thereby indicating a very high level of distress. Control 546 indicates a less severe state, as does respective controls 548, 550, and 552.

FIG. 6 depicts an illustrative user interface that is presented on a first communications device 600. The user interface, generally referenced by numeral 610, includes several user-interface controls that are usable to engage modes or operational actions. For example, a discrete-mode control 612 can be used to put the process into a discreet mode, which would hide additional information that might otherwise be provided if the process were not in the discrete mode. For example, in discreet mode, attribute information associated with the sending computing device would not be sent to the receiving computing device in such a way that it would be understandable by a potentially responsive user. In discrete mode, the method could also mask or encrypt or otherwise hide any personal identifying information or attribute information associated with the user associated with device 600.

Control 614 it is usable to toggle the process out of discrete mode, or otherwise implement a non-discrete mode, in which more identifying information is allowed to be shared with a responsive user.

"Authentication" control 616 is usable too put a device into an authentication mode, such as one that is usable to share an authentication code or image. For example, the distressed user could send an authentication message (which could include a secret image), to a receiving device. When the responsive user shows up and approaches the distressed user, each person can mutually show the secret image or code to confirm that the responsive user is responding to the alert that was communicated by the distressed user.

"Distance" control 618 is usable to present visual map or otherwise show a distance that the responsive user is from the distressed user and vice versa.

"Exclude" control 620 is a control that allows a user of device 610 to indicate one or more people who should be excluded from receiving the alert. For example, a distressed user may have previously indicated that family members should not receive a distress alert. Alternatively or additionally, a distressed user may, in real time, exclude certain people from receiving the distress alert. These are people who might include or have certain attributes. One of the goals or points of this mode is to enable a distressed user to customize who sees the distress alert and or who is able to respond to it. In this way, "respondents attributes" control 622 is usable to configure or denote the previously mentioned attributes that a distressed user would like the responsive user to have in one embodiment.

Likewise, the controls depicted on user interface 610 could also be presented on a user interface of the responsive device. Responding users might also wish to be discreet, enable authentication, view their distance from the distressed user, exclude receiving alerts associated with certain types of distressed users, or only be able to respond to users that have certain attributes. Thus, controls similar to those of user interface 610 could also be presented on the receiving device.

FIG. 7 depicts another illustrative computing device 700 with a user interface that is generally referenced by numeral 712. User interface 712 is an illustrative user interface that is presented on a receiving device in one embodiment. Multiple types of controls could be included. Two illustrative controls are shown, including an "acknowledge" control 714 and an "I'm here" control 716. A responsive user can press the "acknowledge" button 714, which would send an acknowledgement in one embodiment.

In other embodiments, pressing "acknowledge" button 714 could present other options to convey to the distressed user, such as control 714 that indicates the responsive user is on his or her way. Similarly, control 7148 is usable to indicate that a responsive user will be there in a certain amount of time, such as five minutes. In one embodiment, the amount of time can automatically be determined by one or more of the sending or responding computing devices based on the location of the first computing device, second computing device, and the mode of travel that the responsive user will be using to reach the distressed user.

Figure 10:
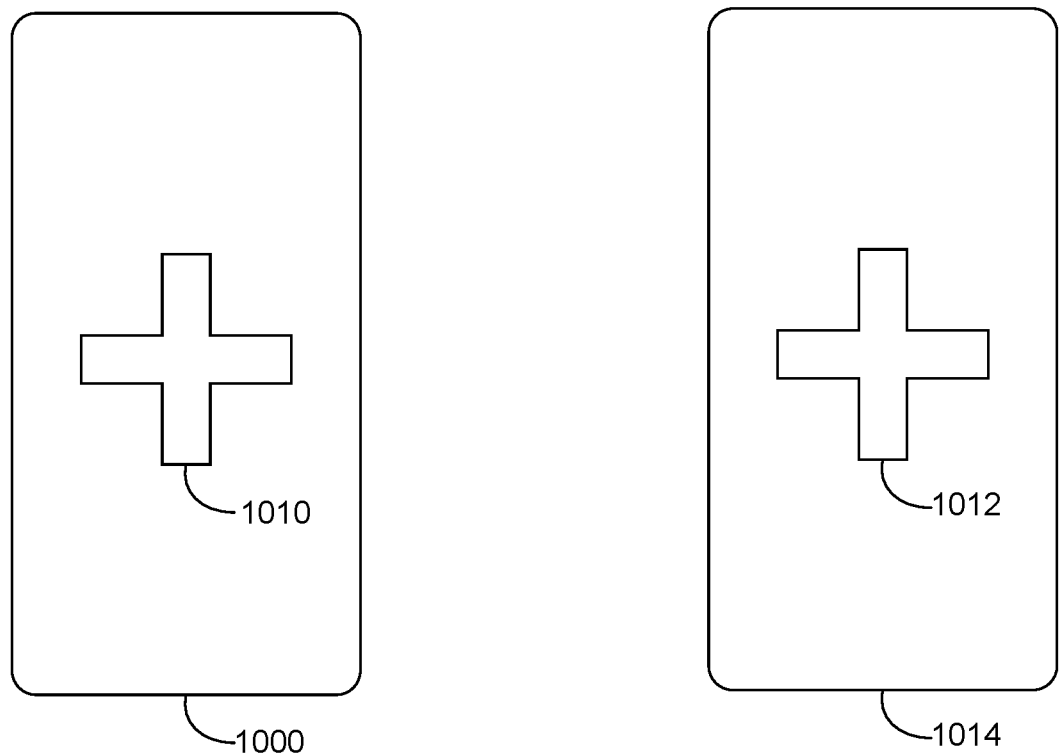
FIG. 10 depicts an illustrative code word (which could include a test image) suitable for helping authenticate a responsive user in accordance with an embodiment of the invention.

If the responsive user would like to convey a different amount of time, that could be accomplished by yet another control, such as control 714C to indicate a 30-minute arrival time. Control 716 is usable to indicate that the responsive user has arrived and is proximately near the distressed user. At that time, the secret images could be disclosed to each other if that option was enabled or selected. For example, the responsive user could show image 1012 to the distressed user, who could also show matching image 1010 (as shown in FIG. 10).

In some embodiments, lamp 312 (shown in FIG. 3) could flash to indicate the computing device associated with the distressed user, to make finding the distressed user easier.

Figure 8:
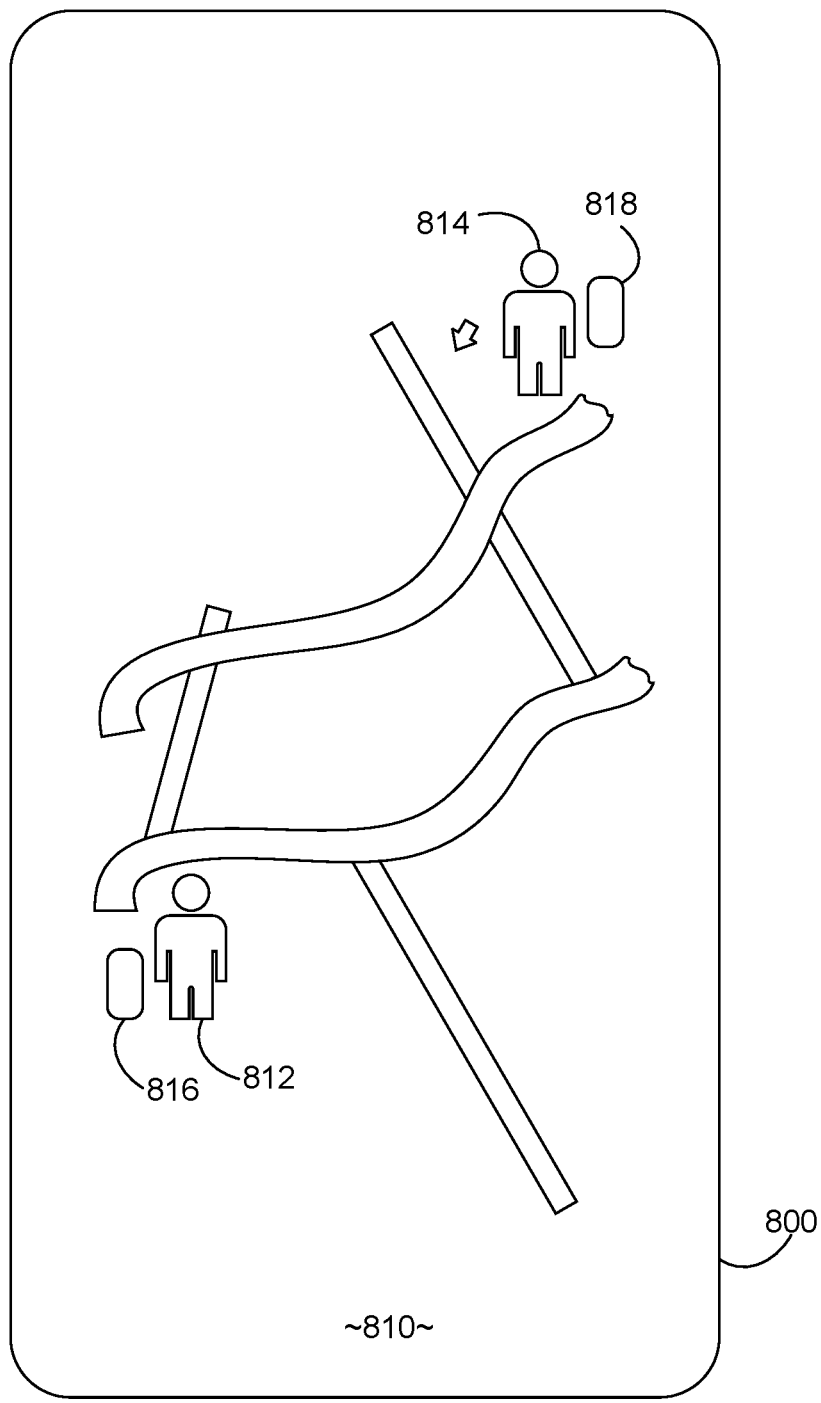
FIGS. 8 and 9 depict illustrative navigation-assistance user interfaces suitable for use in accordance with one or more embodiments of the invention.

FIG. 8 depicts an illustrative map 810 on a computing device 800. The map 810 indicates both the distressed user's location 812 as well as the location of responsive user 814 in one embodiment. The location functionally is enabled by way of a GPS radion in one embodiment. Distressed user 812 is associated with a first computing device 816. Responsive user 814 is associated with a computing device 818. The interface can present a set of directions that is useful to indicate how responsive user should reach distressed user 812. These instructions can be presented visually by way of a map, or in prose by way of instructions.

As the distressed person moves, his or her GPS coordinates are updated on the map in real time. The app can transmit a signal indicate of its location (e.g., using Bluetooth, near-field communication ("NFC"), etc.) to help the responder find the distressed person's computing device. The information can be timestamped and track who responds to the call. The app can alerts persons within a certain area, zip code, or radius. Anyone on the network who wants to help, and is willing to help, can. In one embodiment, persons willing indicate a preference to not receive payment, helping to ensure that only those who genuinely want to help do so. The system can facilitate a bidirectional dialogue if desired. In one embodiment, facial recognition or biometric authentication is employed to authenticate the distressed person. In other embodiments, instead of presenting a map in the form of interface 810, a simpler navigational control could be presented such as that depicted in FIG. 9.

Figure 9:
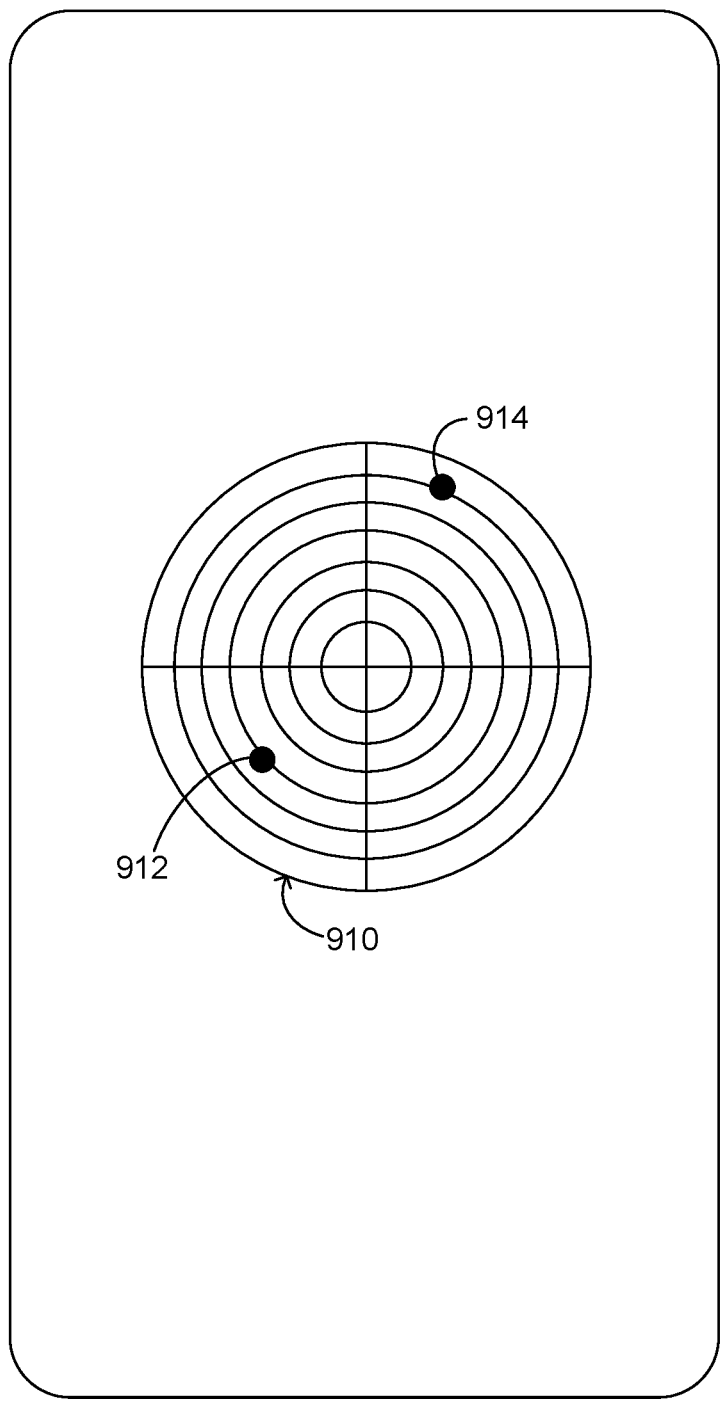

FIG. 9 depicts an alternative location-presentation control 910, which depicts a location of a distressed user 912 as well as a responsive user 914. FIG. 10 depicts an illustrative test image 1010 that is presented on a first computing device 1000. The same image 1012 is presented on a second computing device 1014 so as to provide a higher level of confidence that the responsive user associated with device 1014 is indeed the anticipated user responding to a distress alert that was sent by device 1000. If the images match, that indicates that the responsive user is who he or she purports to be.

Figure 11:
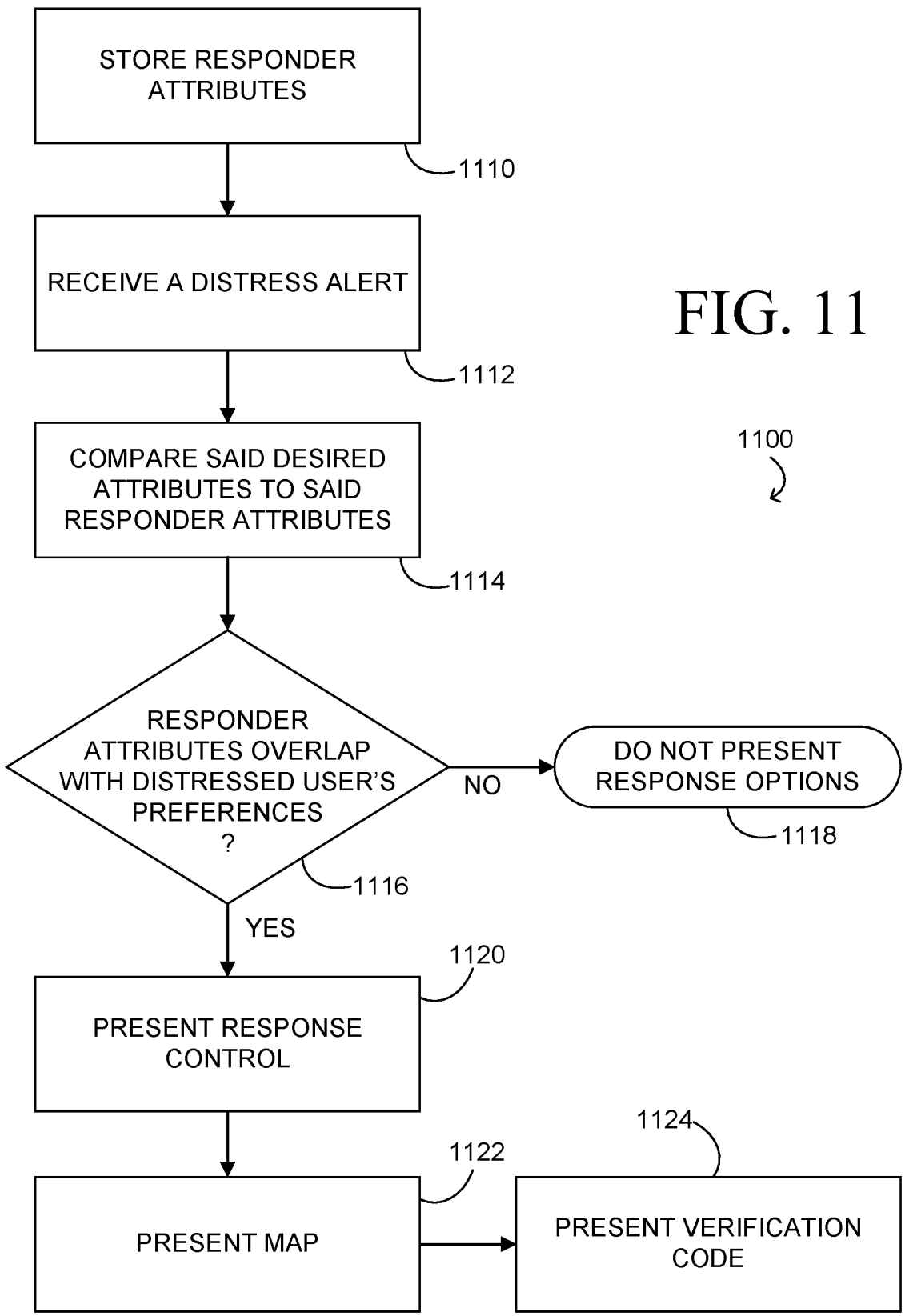
FIG. 11 depicts an illustrative method to help reduce a suicide (including a suicide attempt) in accordance with an embodiment of the invention.

Turning now to FIG. 11 (and with reference to FIG. 2), another illustrative method for carrying out an embodiment of the present invention is provided and referenced generally by the numeral 1100. As mentioned, one embodiment of the invention includes one or more non-transitory computer readable storage media, such as the media referenced in FIG. 1. The storage media store at least one program to assist a distressed person. The program(s) comprise instructions that, when executed by a receiving computing device with a display, a touch-responsive surface and one or more sensors to detect a touch interaction with the touch-sensitive surface, cause the receiving computing device perform a method, which includes, at a step 1110, storing a set of responder attributes, such as in database 210A of computing device 210. The responder attributes are attributes of a user who might respond to a distress alert communicated from a sending computing device (such as device 220) that is associated with the distressed person.

In one embodiment, the method further includes receiving the distress alert from the sending computing device 220 at a step 1112. The sending device 220 would have initiated the communication of the alert to a plurality of devices, e.g., 212-218. The distress alert is an electronic communication sent from the sending computing device 220 in one embodiment. The electronic communication indicates that said distressed person is in a distressed state. The said electronic communication includes a location of the sending computing device 220 and a set of desired attributes associated with said distressed user, which were stored in database 220 in one embodiment. The set of desired attributes indicate preferred attributes of a responder who might respond to said distress alert.

At a step 1114, the set of desired attributes (e.g., from database 22)A) are comparted to the responder attributes (e.g., stored in database 210A) in one embodiment. A determination is made at a step 1116 as to whether the responder attributes overlap with the distressed user's preferences. This can include determining whether there is complete overlap (e.g., all of the distressed user's attributes communicated from device 220 are found in responding user's database 210) or only a subset thereof. If the preferred attributes are not found in the responder attributes, then at a step 1118, processing stops in one embodiment, and the response control(s) are not presented on the display of device 210.

But if the preferred attributes are found in the responder attributes, then at a step 1120, the method further includes presenting on the display of device 210 a response control (such the buttons or controls of FIGS. 3 and 5A-5C) that is useable to receive user input to send an electronic acknowledgment from the receiving computing device 210 to the sending computing device 220. As mentioned, the response control can be presented on the display of the receiving computing device 210. The response control indicates a degree of immediacy that the responder intends to locate said distressed person.

The method also includes continuing with one or more remaining steps recited below. Upon receiving the user input at computing device 210, one embodiment of the method includes sending the electronic acknowledgement to the sending computing device 220.

The desired attributes from database 220 indicate a gender preference in one embodiment.

In one embodiment, the program further causes the receiving computing device 210 to present on said display a directional interface that indicates the location of the first distressed person. The directional interface could be of the type depicted in FIG. 8 or FIG. 9.

The aforementioned electronic communication also includes a verification code in one embodiment. The verification code is useable to confirm that said receiving computing device really did receive said alert. The verification code could be a code (such as a number) or a code in the form or a picture, such as depicted in FIG. 10. The program further causes the receiving computing device to present the verification code on the display, thereby confirming an authenticity of said responder.

An embodiment of the invention provides the ability to scroll through or otherwise search the names of potential responders. The distressed person can indicate preferences for or against potential responders (such as swiping one direction, double tapping, etc. to disqualify a person). In one embodiment, this selection can be confirmed by a user-interface element, such as a check box or "click to confirm" control. Similarly, preferences for potential responders can be indicated (e.g., by swiping a different direction, providing an audible cue, etc.). This favorable indication can be followed by a verification prompt that to confirm a desire to notify the responder. To aid the distressed person's spirits, a favorable selection leads to an audio/visual response by the computing device in one embodiment. For example, the app can present a corny "kazoo" sound and/or display confetti shooting out on display 118.

A problem with current suicide-prevention technologies is that they are impersonable. Sometimes responses can be robotic and programmed, disinterested audio calls, or non-human chat boxes. As mentioned, current help mechanisms are restricted by location and offer little or accountability. The distressed person can be subject to whomever happens to answer the phone call, with no choice or input as to responder's demographic traits or any indication as to whether the responder has been through any shared experiences (enabling a more fruitful help session). The instant invention responds to these shortcomings by providing the potential for a real-time in-person meeting, thereby fostering an environment where the vulnerable person can have a deeper connection and greater potential to open up to a responder (and one with preferred attributes). This can help reduce feelings of judgment or criticism.

One embodiment of the invention provides for a continuous communication from the time the distressed person selects a responder (or otherwise establishes an initial connection with a responder) until the responder shows up. The distressed person is able to see the estimated time of arrival of the responder, as discussed above. In one embodiment, a verifiable picture or password is included to enable verification. The pictures/passwords must mutually correspond with each to verify that the supposed responder is the actual desired responder in one embodiment.

Logging into the application can be expedited by utilizing third-party log-in credentials already associated with the user (e.g., by Google, facebook, Instagram or other such sites). Ultimately the person in distress has an ability to choose from all available candidates as to whom they would like to respond to the distressed signal they initiated in one embodiment.

While principles of embodiments of the invention have been made clear in the above disclosure, those skilled in the art may make modifications in the structure, arrangement, portions and components of the invention without departing from those principles. The description and drawings are interpreted as illustrative and not in a limiting sense except that the invention is given a scope commensurate with the included (or subsequently included) claims.

What is claimed is:

1. One or more non-transitory computer readable storage media storing at least one program to assist a distressed person, the at least one program comprising instructions that, when executed by a receiving computing device with a display, a touch-responsive surface and one or more sensors to detect a touch interaction with the touch-sensitive surface, cause the receiving computing device to:

store a set of responder attributes, wherein said responder attributes are attributes of a user who might respond to a distress alert communicated from a sending computing device, wherein said sending computing device is associated with said distressed person;

receive said distress alert from said sending computing device, wherein said distress alert is an electronic communication sent from said sending computing device, wherein said electronic communication indicates that said distressed person is in a distressed state, and wherein said electronic communication includes a location of said sending computing device and a set of desired attributes associated with said distressed user, wherein said set of desired attributes indicate preferred attributes of a responder who might respond to said distress alert;

compare said desired attributes to said responder attributes;

if said preferred attributes are found in said responder attributes, presenting on said display a response control that is useable to receive user input to send an electronic acknowledgment from said receiving computing device to said sending computing device;

if said preferred attributes are not found in said responder attributes, not presenting said response control on said display;

upon receiving said user input, sending said electronic acknowledgement to said sending computing device.

2. The media of claim 1, wherein said desired attributes indicate a gender preference.

3. The media of claim 2, wherein said response control is presented on said display of said receiving computing device.

4. The media of claim 3, wherein said response control indicates a degree of immediacy that said responder intends to locate said distressed person.

5. The media of claim 1, wherein said program further causes the receiving computing device to present on said display a directional interface that indicates said location of said first distressed person.

6. The media of claim 1, wherein said electronic communication further includes a verification code, wherein said verification code is useable to confirm that said receiving computing device really did receive said alert.

7. One or more non-transitory computer readable storage media storing at least one program to assist a distressed person, the at least one program comprising instructions that, when executed by a receiving computing device with a display, a touch-responsive surface and one or more sensors to detect a touch interaction with the touch-sensitive surface, cause the receiving computing device to:

store a set of responder attributes, wherein said responder attributes are attributes of a user who might respond to a distress alert communicated from a sending computing device, wherein said sending computing device is associated with said distressed person;

receive said distress alert from said sending computing device, wherein said distress alert is an electronic communication sent from said sending computing device, wherein said electronic communication indicates that said distressed person is in a distressed state, wherein said electronic communication includes a location of said sending computing device and a set of desired attributes associated with said distressed user, wherein said electronic communication further includes a verification code, wherein said verification code is useable to confirm that said receiving computing device received said alert;

wherein said set of desired attributes indicate preferred attributes of a responder who might respond to said distress alert;

compare said desired attributes to said responder attributes;

if said preferred attributes are found in said responder attributes, presenting on said display a response control that is useable to receive user input to send an electronic acknowledgment from said receiving computing device to said sending computing device;

if said preferred attributes are not found in said responder attributes, not presenting said response control on said display;

upon receiving said user input, sending said electronic acknowledgement to said sending computing device; and wherein said program further causes the receiving computing device to present on said display said verification code, thereby confirming an authenticity of said responder.

* * * * *